United States Patent [19]
Lieber

[11] Patent Number: 5,078,489
[45] Date of Patent: Jan. 7, 1992

[54] METHOD AND APPARATUS FOR MEASURING OPTICAL ATTENUATION OF AN OPTICAL MEDIUM

[75] Inventor: Winfried Lieber, Kaiserslautern, Fed. Rep. of Germany

[73] Assignee: Siemens Aktiengesellschaft, Munich, Fed. Rep. of Germany

[21] Appl. No.: 394,114

[22] Filed: Aug. 15, 1989

[30] Foreign Application Priority Data

Aug. 23, 1988 [DE] Fed. Rep. of Germany ....... 3828604

[51] Int. Cl.$^5$ .......................................... G01N 21/59
[52] U.S. Cl. ..................... 356/73.1; 385/15
[58] Field of Search ............................ 356/73.1, 323; 350/96.16, 96.2, 96.21, 96.15

[56] References Cited

U.S. PATENT DOCUMENTS

| | | | |
|---|---|---|---|
| 4,618,212 | 10/1986 | Ludington et al. | 356/73.1 |
| 4,652,123 | 3/1987 | Neumann | 356/73.1 |
| 4,714,343 | 12/1987 | Ide | 356/73.1 |
| 4,880,289 | 10/1989 | Imoto et al. | 350/96.16 |

*Primary Examiner*—Vincent P. McGraw
*Assistant Examiner*—LaCharles P. KeeSee
*Attorney, Agent, or Firm*—Hill, Van Santen, Steadman & Simpson

[57] ABSTRACT

A method and apparatus for measuring the optical attenuation of optical mediums characterized by a first transmitter and a second receiver being connected to one output of the optical medium and the second transmitter and first receiver being connected to the other output. Thus, four measuring processes can be obtained, which include measuring the signal from the first transmitter after it passes through the optical medium by the first receiver, measuring the signal from the first transmitter in the second receiver before it passes through the optical medium, measuring the signal from the second transmitter after it has passed through the optical medium by the second receiver and measuring the signal from the second transmitter by the first receiver before it passes through the optical medium. These four values are then processed to determine the exact attenuation of the optical medium.

18 Claims, 4 Drawing Sheets

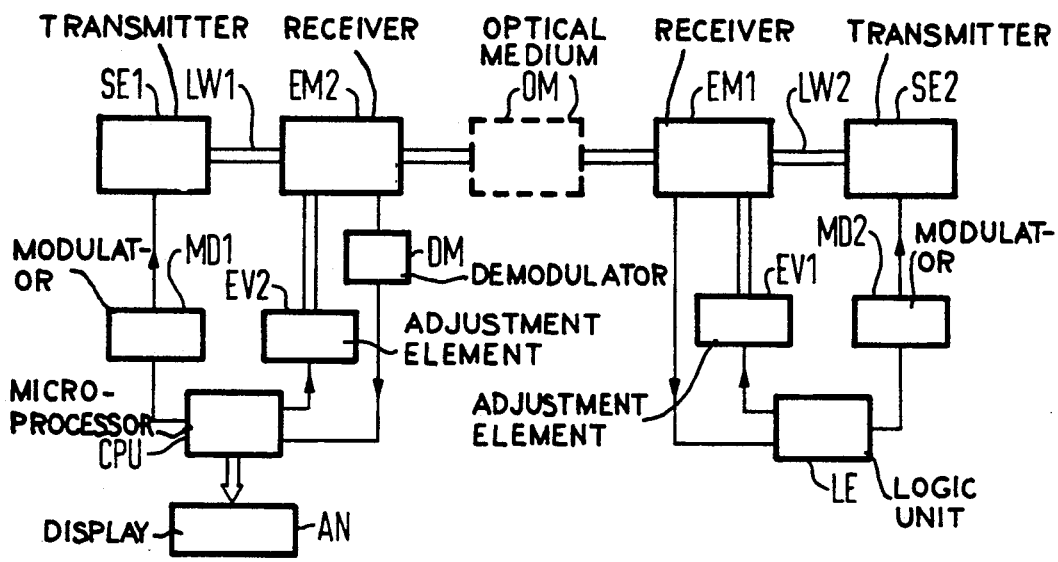
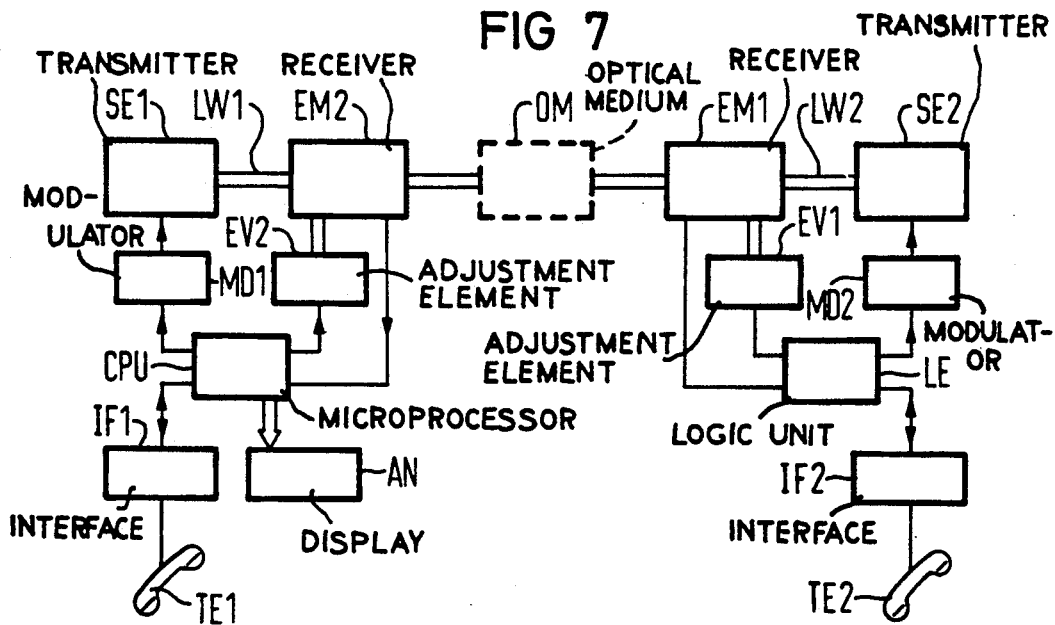

METHOD AND APPARATUS FOR MEASURING OPTICAL ATTENUATION OF AN OPTICAL MEDIUM

BACKGROUND OF THE INVENTION

The present invention is directed to a method for measuring the optical attenuation of an optical medium, whereby an optical measuring signal of a first measuring transmitter or means is coupled into the optical medium and is then coupled out therefrom after traversing the medium and is measured with a first measuring receiver in a first measuring process.

Copending U.S. Patent Application Ser. No. 06/755,276, filed July 15, 1985, claims priority from German Published Application No. 34 29 947 and discloses a measuring device wherein light is coupled from a measuring transmitter into the light waveguide proceeding through a splice location. The light waveguide is thereby guided in a precise, defined fashion in the coupling region so that a largely reproducible coupling relationship can be obtained. In detail, the light to be coupled in is thereby supplied to the actual coupling region by a second light waveguide, whereby a particularly defined and clean in-coupling is achieved.

The optical attenuation of the optical medium, for example of a splice location, of a coupler, of a light waveguide cable or the like, represents an important measured quantity. For example, the optical attenuation, thus, considerably limits the usable product of band width and length of an optical transmission link. Global attenuation measurements, such as, for example the overall attenuation of the optical transmission length, and the attenuation of a sub-link are required. Thus, local attenuation discontinuities can also be added thereto, such as, for example, as occur at an fiber splice, couplers or at other optical components.

Particularly for the employment in optical fibers or, respectively, light waveguide cables, what is referred to as a time-domain reflectometry method and the transmitted light measuring method are known methods for measuring the optical attenuation. The advantages of an optical time-domain reflectometry (OTDR) are that only one end of the light waveguide need be accessible for the measurement. However, a disadvantage of the optical time-domain reflectometry method is the quickly decreasing measuring precision which will occur with increasing distance from the in-coupling location. In the transmitted light method, both ends of the light waveguide must be simultaneously accessible; however, a higher measuring precision, when compared to an optical time-domain reflectometry, will occur. Thus, this measuring method is utilized in the laboratories and in quality protection programs. The measurement with the transmitted light method requires a reference measurement that is acquired in a known fashion by cutting the specimen of the light waveguide back. In addition to the fact that this method is time-consuming and does not work destruction-free, the repeated coupling of the cut-back light waveguide to the respective receiver also limits the obtainable measuring precision.

The measurement of local attenuation discontinuity, for example at a splice location, is generally executed with the assistance of an optical time-domain reflectometry. In practice, however, it must be assumed that the precise measurement of the attenuation discontinuity requires an application of the optical time-domain reflectometry at each of the two light waveguide ends because of the unavoidable tolerances in the radial refractive index geometry of the fibers of the optical light waveguide fibers and because of the unsteadiness of the field diameter proceeding therefrom at the fiber joint. A further disadvantage is also that the measuring precision is dependent on the distance between the joint and the in-coupling location of the measuring signal. Measurements of, for example, the splice attenuation with the transmitted light method is, however, without practical significance because of the reference measurement that is required.

In the measuring method of the above-mentioned U.S. Patent Application, only the out-coupled power following, for example, the splice location is not measured and the quantity of the in-coupled power at the transmission side, however, is not measured. A corresponding measuring device for the thermic splicing enables an estimate of the splice attenuation with relatively precise values when identical light waveguides are employed and given the assumption of a coupling optic having ideal fiber end faces and an ideal arrangement of fiber cores. The splice attenuation $\alpha$ is defined by the measuring of the power modification $\Delta\alpha$ proceeding and following the production of the splice connection upon additive consideration of the mean air splice attenuation of the ideal coupling optics. The following relationship thereby applies:

$$\alpha = \text{mean air splice attenuation} + \Delta\alpha \text{ (dB)}.$$

In practice, the necessary assumptions cited above are not always met with the high precision that is required, as a result whereof the adding of a constant, means air splice attenuation can lead to faulty values. Intrinsic losses, which occur given the mismatching of non-identical light waveguides, are thereby not measurable. Added thereto is that the attenuation of fiber splices that have already been produced, i.e., of a finished fiber splice, cannot be identified with such a method.

SUMMARY OF THE INVENTION

The object of the present invention is to create a method for measuring the optical attenuation of an optical medium that allows a high precision attenuation measurement in a simple way. In accordance with the present invention, this object is achieved by conducting four measuring processes which are a first process which includes passing a first measuring signal from a first transmitter means through the optical medium and measuring the first signal by a first receiver on the other side, a second process which includes passing a second optical measuring signal of a second measuring transmitter or means through the optical medium in an opposite direction and measuring this additional optical signal in a second measuring means, a third measuring process measures the signal of the first measuring transmitter means which is coupled out of the first light waveguide without passing through the optical medium and is measured by the second measuring receiver and a fourth measuring process wherein the measuring signal of the second measuring transmitter means is measured in the first measuring receiver means without passing through the optical medium; and that these four measure values obtained in this way are utilized for identifying the attenuation of the optical medium.

The invention, thus, avoids involved referencing, such as, for example, cutting the light waveguide back and the new coupling problems resulting therefrom. The method of the invention is independent of the manner by which the optical power is coupled in. Over and above this, the universal validity of the method enables a measurement of the optical attenuation for a multitude of applications, for example, for light waveguides, for light waveguide links, for coupling optics, for optical splices, for plug-in connections, for voids in fibers, etc. Every passive optical component can, thus, be utilized as an optical medium and, thus, as a measuring subject. The idealization of the coupling location that is otherwise not always practically suited is eliminated and the invention, likewise, need not be assumed that knowledge of the power modifications during the splicing event is present. A measurement of the splice attenuation of fiber splices that are already produced is, thus, possible in a simple and reliable fashion.

The method of the invention can be employed with particular advantages when the in-coupling and out-coupling of the measuring signals are undertaken upon application of the curvature method because of the measuring process at the transmission side, as well as at the reception side, can then be carried out in an especially easy fashion. The in-coupling and out-coupling of the measuring signals of the type disclosed in the above-mentioned U.S. Patent application can be utilized with particular advantage within the framework of the invention.

The invention is also direction to an apparatus for the implementation of the method of the invention that is characterized in that measuring transmitter means and measuring receiver means are provided for making the measurement. Preferably a transmitter means and a receiver means are provided on each side of the optical medium.

Other improvements of both the method and the apparatus will be readily apparent from the following description of the preferred embodiments, the drawings and claims.

BRIEF DESCRIPTION OF THE DRAWINGS

FIG. 6 is a box diagram of a modification of the measuring equipment of FIG. 1, which modification enables the measurement of the spatially extensive test subjects, for example optical cables; and FIG. 7 is a modification of the box diagram of FIG. 6 comprising additional optical telephones.

DESCRIPTION OF THE PREFERRED EMBODIMENTS

Figure 1:
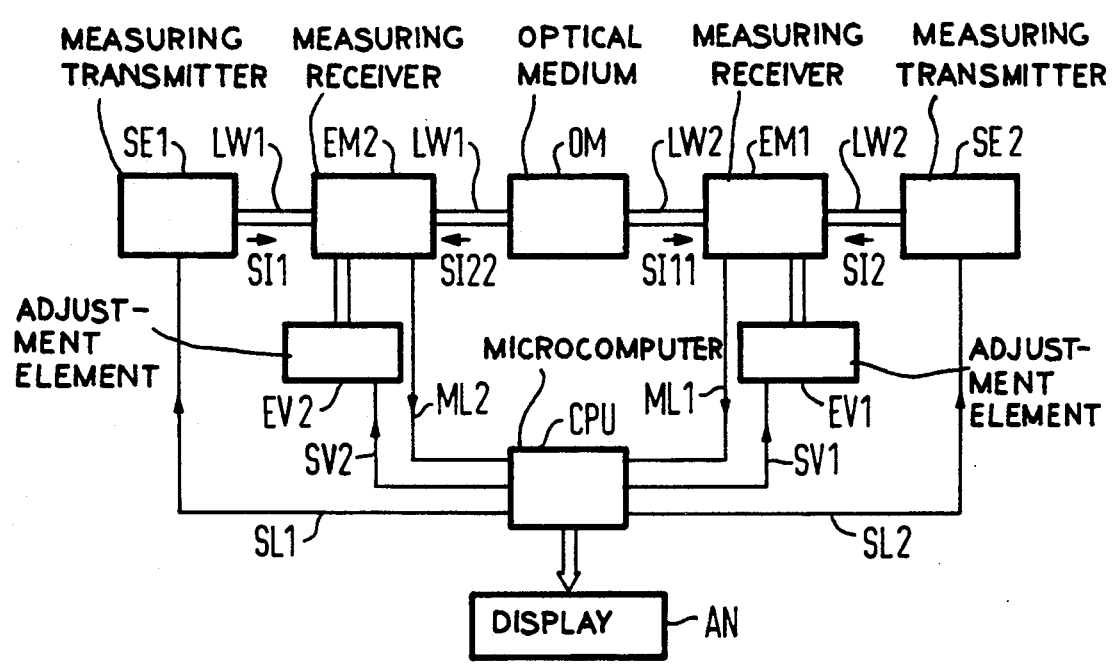
FIG. 1 is a block diagram showing the overall structure of the measuring device in accordance with the present invention for accomplishing the method of the present invention.

The principles of the present invention are particularly useful when incorporated in a method for measuring the optical attenuation of an optical medium OM, which method utilizes the apparatus illustrated in the box diagram of FIG. 1. The optical medium OM, whose transit attenuation is to be identified, can be, for example, composed of a splice location of two light waveguides, of a coupler, of a light waveguide of greater length, of a light waveguide cable or of some other passive optical component. An input light waveguide LW1 is connected to the input side of the optical medium OM and an output waveguide LW2 is connected to the output side of the optical medium. In the case of the optical medium OM, which itself contains a light waveguide, for example in measuring a splice location or when measuring a long light waveguide length, the light waveguides LW1 and LW2 can be formed by a final length or end portion of the light waveguides belonging to the optical medium or, respectively, representing this optical medium. Thus, additional optical waveguide sections are not required. In other instances, light waveguide sections are provided that are expediently provided with corresponding plug-in connectors for connection to the optical medium and, potentially, for connection to the measuring transmitters.

A first measuring transmitter SE1, which forms first transmitting means for transmitting a first optical signal, is provided on the light waveguide LW1 on the left-hand side of the optical medium OM. This first measuring transmitter SE1 is followed by a second measuring receiver EM2, which forms second receiver means for receiving an optical signal moving in the light waveguide LW1. As illustrated, the light waveguide LW2 is connected to the right side of the optical medium OM and on the output thereof and has a first measuring receiver EM1 forming a first receiver means for receiving an optical signal traveling in the light waveguide LW2, and this is followed by a second measuring transmitter SE2 which forms a second transmitter means for transmitting a signal into the light waveguide LW2.

A traditional microprocessor or microcomputer CPU is provided for the control of the various measuring processes. The measuring signals, which are converted into electrical signals in a known fashion in the optical receivers EM2 and EM2, are supplied to the microcomputer CPU via multi-leads ML1 and ML2. Preferably, the optical receivers EM1 and EM2 form an electrical signal in a digitalized form, which will be ready for evaluation in the microcomputer CPU. The microcomputer CPU controls the program execution of the overall measuring process to which end control lines SL1 and SL2 are conducted from the microcomputer CPU to the measuring transmitters SE1 and SE2 via which the alternate activation of the two measuring transmitters is carried out, preferably with a digitalized measuring instruction. It is assumed in the present example that the adjustable curvature coupler, as disclosed in the above-mentioned copending U.S. application, is utilized for the coupling. To this end, it is necessary to bend the light waveguide LW1 or, respectively, LW2 a corresponding curvature in order to enable an in-coupling or, respectively, out-coupling of the measuring signal. Electro-mechanical adjustment elements EV1 and EV2, which are driven via control lines SV1 and SV2 that extend from the microprocessor CPU are provided for actuation of the corresponding adjusting events. The coupling of the measuring receivers EM1 and EM2 to the respective light waveguides LW1 and LW2 is controlled by these electro-mechanical adjustment elements. Particularly for automated measuring processes, it is possible to work with motor operators or with electromagnetic setting elements for this purpose that initiates the in-coupling or, respectively, out-coupling by closing or, respectively, opening a bending bar. This coupling, however, can also occur in the same fashion as in the known thermic splicing apparatus X30 of Siemens AG, namely by manually closing and opening the coupler. The measured quantities that are identified as a result of the measuring process and are supplied to the microprocessors CPU via the measuring lines ML1 and ML2 are subjected to appropriate processing therein and the results are displayed in a display unit AN or, respectively, are printed out or documented in some other way.

Four measuring processes are executed in succession with the measuring arrangement shown in FIG. 1. These four measuring processes are set forth in detail below. It is thereby possible to point out that the sequence of these measuring processes need not occur in the fashion set forth below but, on the contrary, all four measuring processes can be carried out in any random sequence.

First Measuring Process

To perform the first measuring process, only the first measuring transmitter SE1 and the first measuring receiver EM1 are connected to the optical medium OM. The measuring signal SI1 is, thus, coupled out from the measuring transmitter SE1 and is supplied to the optical medium by the light waveguide LW1. This measuring signal SI1 proceeds to the measuring receiver EM1 as a measuring signal SI1 and supplies a measured value at this receiver, which value is transmitted by the measuring line ML1 to the microprocessor CPU.

Figure 2:
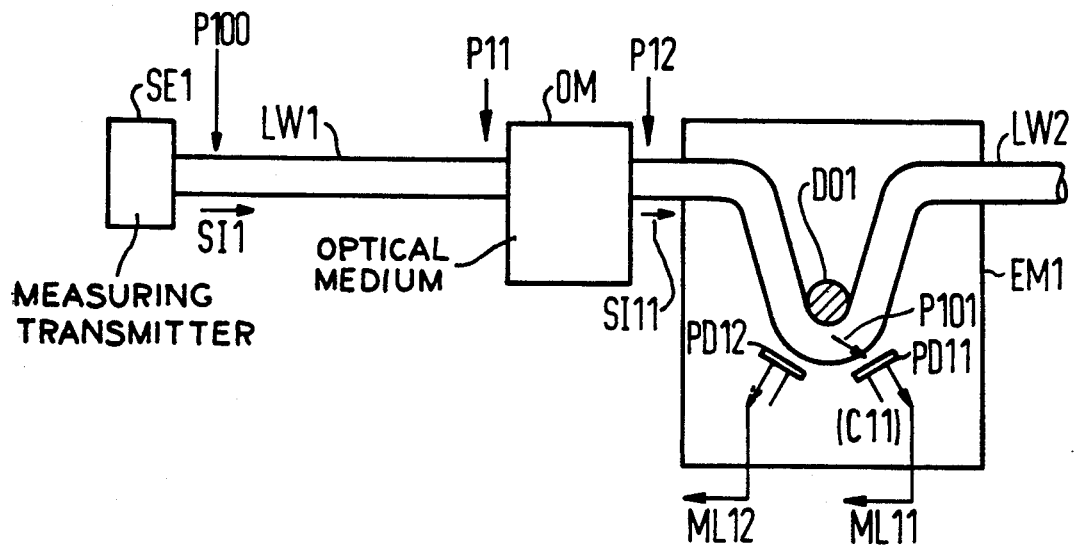
FIGS. 2-5 diagrammatically illustrate the respective coupling arrangements for making the four different discrete measurements.

The corresponding operating conditions for the first step are shown in FIG. 2, wherein the measuring transmitter SE1 is connected to the optical medium OM by the light waveguide LW1 and wherein the second measuring receiver EM2 of FIG. 1 has been omitted. At the output of the optical medium OM, the first measuring receiver EM1 is coupled to the light waveguide LW2, namely in that the light waveguide LW2 is correspondingly curved with an arbor DO1. The power level of the measuring signal emanating from the first measuring transmitter EM1 is referenced P100 and a corresponding part thereof is coupled out in the region of the curvature of the light waveguide LW2 and proceeds to a first photodiode PD11, where it is available as a power level having the size P101. The power level P101 is correspondingly weaker than the power level P100 at the transmission side and, in addition to containing all of the transmission and coupling attenuations, also contains a transit attenuation of the optical medium OM as a critically measured value. The measuring signal P101 is converted into electrical signals, which are not shown in greater detail herein, and are supplied to the microcomputer or microprocessor CPU in this form by the measuring line ML11 for further evaluation. The second measuring transmitter SE2 and the second measuring receiver EM2 are not connected or, respectively, are not activated in this operating condition.

The power level at the input of the optical medium OM is reference P11 and at the output is reference P12. Let the out-coupling attenuation of the first receiver EM1 be C11.

A second photodiode PD12 of the first receiver EM1, thereby, normally does not receive any signals, since the measuring signal P101 is traversing the light waveguide LW2 from the left to the right, as illustrated in FIG. 2. If, however, reflections do occur, for example from the right-hand end of the light waveguide LW2, then a part thereof would be coupled out to the second photodiode PD12. However, it is known in the microprocessor CPU that the second measuring line ML12 supplies a reflected or undesired signal in this measuring process and this is not admitted or, respectively, provided for evaluation. The above considerations apply analogously to the respective second diode in the following FIGS. 3 and 5.

Second Measuring Process

Figure 3:
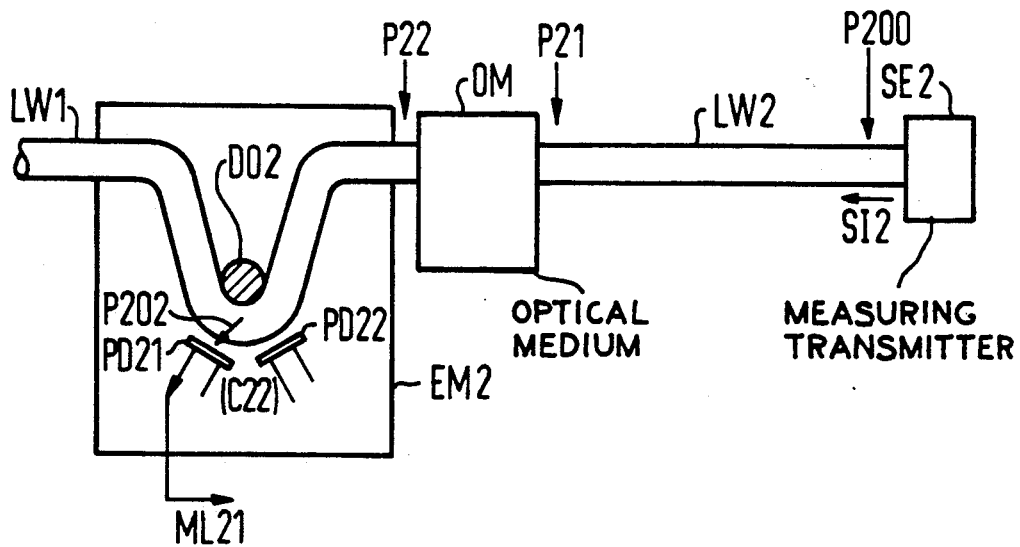

In the second measuring process, the second measuring transmitter SE2 is connected to the light waveguide LW2 and the first measuring receiver EM1 is uncoupled so that the measuring signal SI2 proceeds in the light waveguide LW2 to the optical medium OM and then in the waveguide LW1 to the second measuring receiver EM2. The first measuring transmitter SE1 is not activated during this measuring process. FIG. 3 shows the operating condition for the second measuring process in detail, wherein the measuring transmitter SE1 couples the power level P200 into the light waveguide LW2, this power level P200 proceeds to the second measuring receiver EM2 after passing through the optical medium OM. The coupling of this second receiver EM2 occurs analogous to that of the above-mentioned measuring receiver EM1 of FIG. 2, for example includes an arbor D02 which is provided that curves the light waveguide LW1 such that a corresponding part of the measured signal P200 of the measuring transmitter E21 is coupled out by the arbor D02 as a consequence of the curvature and is supplied to the photodetector PD21. The second measuring signal obtained in this way is converted into an electrical signal (not shown in greater detail) and is conducted via measuring lines ML21 to the microprocessor CPU as a second power level P202. In addition to the standard influencings due to the attenuation of the light waveguides LW2 and of a part of the light waveguide LW1 and the coupling attenuation, the measured signal also contains the transmission attenuation of the optical medium OM. In contrast to the arrangement in FIG. 2, the measurement herein is carried out in the opposite direction, i.e. from right to left.

The power level at the input of the optical medium OM is reference P21 and the power level at the output is reference P22. Let the out-coupling attenuation of the second receiver EM2 be C22.

Third Measuring Process

In the third measuring process, the measuring signal SI1 of the first measuring transmitter SE1 is supplied directly to the second measuring receiver EM2 without passing through the optical medium OM. This means that the first measuring receiver EM1 and the second measuring transmitter SE2 at the right-hand side of the optical medium OM1 of FIG. 1 are not activated.

Figure 4:
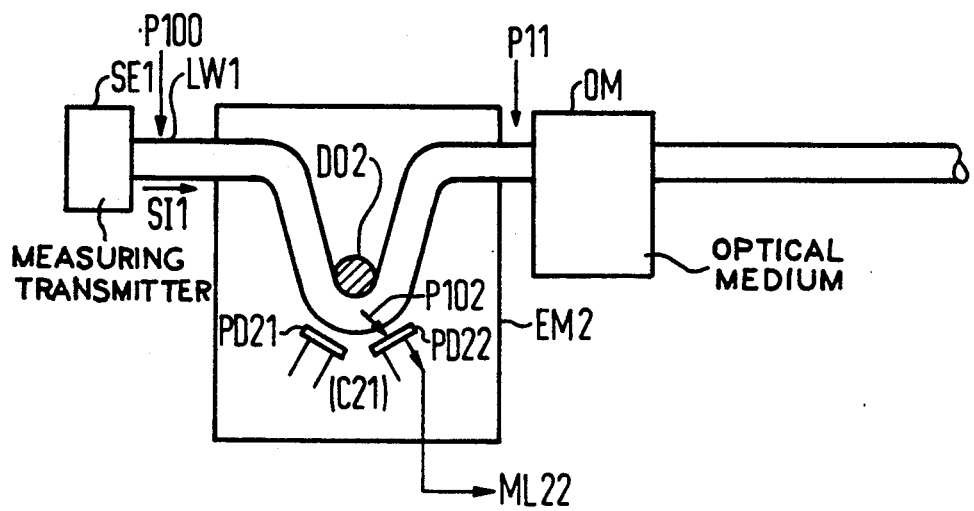

Details regarding this may be seen from FIG. 4, wherein the transmission signal having a power level of P100 is coupled into the light waveguide LW1 by the measuring transmitter SE1 and a part of this measuring signal, which will be diminished by the transmission attenuation of the corresponding section of the light waveguide LW1, is coupled out at the coupling location generated by the arbor D02 and is supplied to the photodiode PD22 of the second receiver. This coupled-out light will have a signal level P102 and will be subject to the output coupling attenuation C21 of the second receiver with the second diode PD22. This signal level is converted into corresponding electrical signals and is then supplied to the microprocessor CPU via the measuring lines ML22.

Fourth Measuring Process

In the operating mode of the fourth process, only the part to the right of the optical medium OM in FIG. 1 is activated. Thus, the second measuring transmitter SE2 is connected to the light waveguide LW2 and the measurement is carried out with the first measuring receiver EM1. The measuring devices SE1 and EM2 to the left of the optical medium OM of FIG. 1 are not activated.

Figure 5:
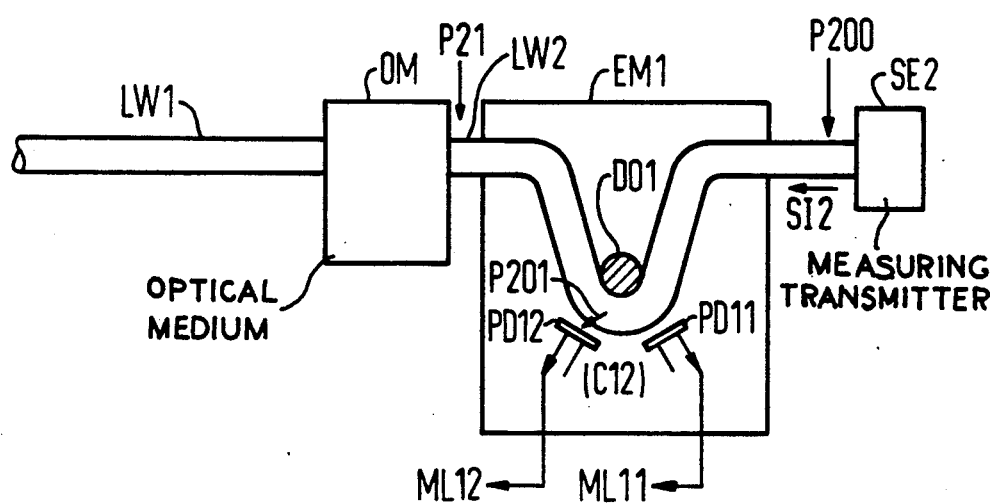

The details regarding this fourth process are shown in FIG. 5, wherein the second measuring transmitter SE2 supplies a measuring signal having a level P200 into the light waveguide LW2. A corresponding part defined by the arbor DO1 is coupled out at the coupling location, due to the curvature of the light waveguide LW2 and is subjected to an out-coupling attenuation C12. The out-coupled part proceeds to the photodetector PD12, whereby the corresponding level value is referenced P201. After conversion into electrical signal, this level value proceeds via the measuring line ML12 to the microprocessor CPU and is available there as a fourth measured value.

Proceeding from the measured quantities entered in FIGS. 2-5, the following relationships occur for the coupling efficiency $\eta$ of the optical medium OM:

$$\eta = \frac{P22}{P21} \quad \text{(Figure 3)}$$

or $$\eta = \frac{P12}{P11} \quad \text{(Figure 2)}$$

The values of the measured signals that are respectively out-coupled with the out-coupling efficiencies C11, C12, C21 and C22 of the receivers EM1 and EM2, which are shown in FIGS. 2-5. It is thereby considered that the value pairs C21 and C22, as well as C11 and C12, are respectively identical, given a symmetrical structure of the respective bending coupler arrangement If they are different, for example given an asymmetric structure, then the respective relationship $$\frac{C21}{C22} \text{ and } \frac{C12}{C11}$$

can be identified by a one-time measuring process and can then be permanently stored in the microprocessor CPU.

The following relationships apply in detail:

$$P101 = P12 \cdot C11;$$

$$P202 = P22 \cdot C22;$$

$$P102 = P11 \cdot C21; \text{ and}$$

$$P201 = P21 \cdot C12.$$

A resolution of the above equation system supplies the following relationship:

$$\eta = \sqrt{\frac{P202 \cdot P101}{P102 \cdot P201}} \cdot \sqrt{\frac{C12 \cdot C21}{C22 \cdot C11}}$$

$\alpha = -10 \cdot \log \eta$ (db) is valid for the attenuation $\alpha$.
The expression is:

$$\frac{C12 \cdot C21}{C22 \cdot C11} = 1$$

given symmetrical couplers and the simplified relationship of:

$$\alpha = -10 \cdot \log \sqrt{\frac{P202 \cdot P101}{P102 \cdot P201}} \quad (db)$$

derives for the attenuation. The transit attenuation $\alpha$ of the respective optical mediums OM can, thus, be exactly identified from the four measuring processes without any restriction whatsoever, due to the simplified assumption and other approximation solutions. As already mentioned, the sequence of the individual measurements is thereby arbitrary if only the four measured vales P101, P102, as well as P201 and P202, required overall are separately identified, as set forth in detail with regard to the descriptons of FIGS. 2-5.

An embodiment for the measuring of the attenuation of the optical medium M, given local separatoin of the connections of this medium, for example for the measurement in a cable link or at a long fiber length or the liek, is shown in FIG. 6. Since the input and output of the optical medium OM lie at spatially different locations, modules in addition to the individual elements shown in FIG. 1, which have been reference with the same element numbers, are required in order to be able to implement such a remote measurement. A logic unit LE that is controlled by instruction signals that are supplied by the microprocessor CPU is present on the right-hand side of the optical medium OM. Corresponding to the respective measuring processes, the second transmitter SE2 and the first receiver EM1 are controlled by this logic unit LE and are connected to the light waveguide LW2. The control instructions are transmitted to the logic unit LE with the transmission signal of the first transmitter SE1 to which end the signal source SE1 must be correspondingly modulated. In detail, a modulator MD1 connected to the microprocessor CPU is provided for this purpose, and this modulator MD1 causes the corresponding modulation of the transmission signals of the measuring transmitter SE1. The modulator MD2 is provided in analogous fashion at the right-hand end of the optical medium OM, and this modulator MD2 is driven proceeding from the logic unit LE and modulates the output of the second transmitter SE2 such that the level values received by the measuring receiver EM1 are transmitted to the left-hand end of the optical medium OM in an appropriately coded form by modulation of the transmission signal of the measuring transmitter SE2. The demodulation of these measured values occurs by a demodulator DM following the second receiver EM2, whose measured values then are available for evaluation in the microprocessor CPU in a fashion analogous to the exemplary embodiment of FIG. 1.

Another embodiment illustrated in FIG. 7 modifies the measuring arrangement of FIG. 6 so that the respective telephones TE1 and TE2 are additionally present at each of the two sides. The telephone TE1 is connected to the microprocessor CPU by an interface IF1, whereas the telephone TE2 is connected to the logic unit LE by an interface IF2. When the optical medium OM is a light waveguide cable or a long light waveguide fiber or, respectively, a light waveguide, a communication from one end to the other with the optical signal is possible in this fashion.

The invention allows a series of modifications. For example, the separate diodes of FIGS. 2-5 can be replaced by a single, large area diode. This, however, assumes that no undesirable reflected signals occur that would possibly falsify the results of the measurement In addition, the logic unit LE of FIGS. 6 and 7 can, likewise, be formed by a microprocessor, whereby the control can occur from both sides of the embodiment shown in FIG. 6 or, respectively, FIG. 7, dependent upon the application.

Given outputs of the optical medium OM that lie spatially close to one another (for example at the splice location), it can also be adequate to provide a total of only a single measuring transmitter and of only a single measuring receiver. In this case, the measuring transmitter and measuring receiver must be connected to the left end or, respectively, the right end of the optical medium OM and respective alternation, namely according to the configuration as shown in FIGS. 2-5, wherein, of course, only one element, namely the respective transmitter and the respective receiver, are actually respectively active, whereas the two others are kept in their non-active condition.

Of course, other known coupling devices can be used for coupling the measuring signal out instead of the illustrated bending couplers. Bending couplers, however, have the advantage that no prepared fiber end faces are required and that the problem always connected therewith can be avoided. This also creates the possibility of making measurements at a through-fiber or, respectively, at a through-light waveguide without these having to be tailored or, respectively, prepared.

In general, one proceeds such in the invention that the transmitters SE1 and SE2 are connected to the end faces of the light waveguides LW1 or, respectively, LW2, whereas the receivers EM1 and EM2 are to be connected by couplers. However, it is also possible to implement a coupling for the transmitters SE1 and SE2 utilizing bending couplers analogous to the coupling methods shown in FIGS. 2-5 with other type couplers. In the employment of bending couplers analogous to FIGS. 2-5 is of great practical significance for measuring local attenuation discontinuities that occur, for example, in fiber splices. The universal validity of the method of the invention allows an arbitrary combination of direct in-coupling and in-coupling with curvature methods at both measuring transmitters, dependent upon the embodiment.

The optical frequency of the first measuring transmitter SE1 and of the second measuring transmitter SE2 expediently lies within a frequency band of interest for the transmission. The two measuring frequencies of the two measuring transmitters SE1 and SE2 are expediently selected to be different.

Although various minor modifications may be suggested by those versed in the art, it should be understood that I wish to embody within the scope of the patent granted hereon all such modifications as reasonably and properly come within the scope of my contribution to the art.

I claim:

1. A method for measuring optical attenuation of an optical medium comprising the steps of performing a first measuring process by coupling in a first optical measuring signal of a first optical transmitter to pass through the optical medium and coupling the signal out and measuring the signal in a first measuring receiver; performing a second measuring process by coupling a second optical measuring signal form a second optical transmitter to pass through the optical medium in the opposite direction and coupling out the second optical signal after passing through the optical medium and measuring this second signal in a second measuring receiver; performing a third measuring process by coupling in the first signal and coupling it out without passing through the optical medium to be measured by the second measuring receiver; performing a fourth measuring process by coupling in the second measuring signal from the second transmitter and coupling it out without passing through the optical medium and measuring in the first measuring receiver; then utilizing the four measured values obtained by the four processes for identifying the attenuation of the optical medium; and for measurements of a spatially extended optical medium including adding steps of modulating the second signal of the second transmitter by a measured signal received by the first measuring receiver; transmitting the modulated signal of the second transmitter by the optical medium to the second receiver; and demodulating the modulating signal received by the second optical receiver.

2. A method according to claim 1, wherein the in-coupling and out-coupling of the measuring signals is undertaken by in-coupling and out-coupling the signals from light waveguides.

3. A method according to claim 2, wherein the in-coupling and out-coupling of the measuring signals is undertaken in short light waveguide sections which are arranged preceding and following the optical medium.

4. A method according to claim 2, wherein the in-coupling and out-coupling of the measuring signals is undertaken according to a curvature method of coupling.

5. A method according to claim 2, wherein the optical measuring signal is coupled from the respective transmitter via the end faces of fiber ends of the respective light waveguides and that the measuring receivers are coupled to the light waveguides according to the curvature method.

6. A method according to claim 1, wherein the optical frequency of the first measuring signal and the second measuring signal lie within the optical frequency interval of interest for the transmission technology.

7. A method according to claim 6, wherein the measuring frequency of the two measuring signals are selected to be different.

8. A method according to claim 1, which includes providing optical telephone connections for each of the measuring equipments with electrical interface and telephone connections.

9. A method according to claim 1, which includes repeating each of the measuring processes and forming a mean value to produce an improvement in the measuring precision.

10. An apparatus for implementing a method of measuring the optical attenuation of an optical medium, said apparatus comprising;
means for performing a first measuring process by passing a first optical measuring signal through the optical medium in a first direction, including a first measuring transmitter coupled to a first end of the optical medium to couple in the first optical measuring signal and a first measuring receiver coupled to a second end of the optical medium for coupling the first optical measuring signal out and measuring the coupled out signal, means for performing a second measuring the coupled out signal, means for performing a second measuring process by passing a second optical measuring signal through the optical medium in a second opposite direction, including a second measuring transmitter coupled to the second end of the optical medium for coupling in a second optical measuring signal and a second measuring receiver coupled to the first end of said optical medium for coupling the second measured signal out and measuring the second coupled out signal, means for performing a third measuring process by transmitting the first signal from the first transmitter to the first receiver without passing the signal through the optical medium and measuring the first signal in the first measuring receiver; means for performing a fourth measuring process by transmitting the second measuring signal from the second transmitter to the second receiver without passing the second signal through the optical medium and measuring the second signal in the second measuring receiver and thereby obtaining four measured values from the four preceding means; means for then utilizing the four measured values for identifying the attenuation of the optical medium; and means for measuring a spatially extending optical medium including adding means for modulating the second signal of the second transmitter by a measured signal received by the first measuring receiver, means for transmitting the modulated signal of the second transmitter through the optical medium to the second receiver, and means for demodulating the modulating signal received by the second receiver; each of said receivers having bending couplers for forming the coupling to an optical waveguide.

11. An apparatus according to claim 10, wherein each of the bending couplers has two reception diodes, with one diode receiving signals coupled out in one direction and the second diode receiving signals coupled out in the opposite direction.

12. An apparatus according to claim 10, wherein each of the bending couplers has a single diode constructed in size and symmetry to receive signals travelling in both directions in said optical waveguide.

13. An apparatus according to claim 10, wherein actuating means are provided for activating the bending couplers, said bending couplers being capable of being coupled to the respective optical waveguides with said activating means.

14. An apparatus according to claim 10, wherein each of the receivers is connected to a optical waveguide which is coupled to the optical medium by plug connectors.

15. An apparatus according to claim 10, wherein each of the transmitters are connected to an end face of a optical waveguide, which is provided for coupling the measuring transmitters to the optical medium.

16. An apparatus according to claim 10, wherein the outputs of the optical medium are coupled to the respective measuring transmitters and receivers by correspondingly long optical waveguide sections.

17. An apparatus for implementing a method of measuring the optical attenuation of an optical medium, said apparatus comprising:

means for performing a first measuring process by passing a first optical measuring signal through the optical medium in a first direction, including only a single measuring transmitter to couple in the first optical measuring signal to a first end of the optical medium and a single measuring receiver for coupling the first optical measuring signal out from a second end of the optical medium and measuring the first coupled out signal and means to selectively couple said single measuring transmitter and said single measuring receiver in an arrangement at opposite ends of the optical medium to make a first measurement, said means to selectively couple including bending couplers to form the coupling to the optical waveguide, means for performing a second measuring process by passing a second optical measuring signal through the optical medium in a second opposite direction, including said single measuring transmitter for coupling in a second optical measuring signal to the second end of the optical medium and said single measuring receiver for coupling out the second measured signal out from the first end of said optical medium and measuring the second coupled out signal and means to selectively couple said single measuring transmitter and said single measuring receiver in an arrangement at opposite ends of the optical medium to make a second measurement.

means for performing a third measuring process by passing a said first optical measuring signal in said first direction directly from said single measuring transmitter to said single measuring receiver without passing said first measuring signal through the optical medium and measuring the first measuring signal in said single measuring receiver to make a third measurement, means for performing a fourth measuring process by passing a said second optical measuring signal in said second, opposite direction directly from said single measuring transmitter to said single measuring receiver without passing said second measuring signal through the optical medium and measuring the second measuring signal in said single measuring receiver to make a fourth measurement and thereby obtaining four measured values from the four preceding means; means for then utilizing the four measured values for identifying the attenuation of the optical medium.

18. A method for measuring optical attenuation of an optical medium comprising the steps of performing a first measuring process by coupling in a first optical measuring signal of a first optical transmitter to pass through the optical medium and coupling the signal out and measuring the signal in a first measuring receiver; performing a second measuring process by coupling a second optical measuring signal from a second optical transmitter to pass through the optical medium in the opposite direction and coupling out the second optical signal after passing through the optical medium and measuring this second optical signal in a second measuring receiver; performing a third measuring process by coupling in the first optical measuring signal and coupling it out without passing through the optical medium to be measured by the second measuring receiver; performing a fourth measuring process by coupling in the second optical measuring signal from the second optical transmitter and coupling it out without passing through the optical medium and measuring in the first measuring receiver and then utilizing the four measured values obtained by the four processes for identifying the attenuation of the optical medium, the optical frequency of the first optical transmitter and of the second optical transmitter being within a frequency band of interest for the transmission and the frequencies of the two optical signal of the two optical transmitters being selected to be different.

* * * * *